US008051991B2

(12) United States Patent
Krause et al.

(10) Patent No.: US 8,051,991 B2
(45) Date of Patent: Nov. 8, 2011

(54) PLASMA SEPARATION MEMBRANE (75) Inventors: Bernd Krause, Rangendingen (DE);
Markus Hornung, Nehren (DE);
Herman Goehl, Bisingen (DE)

(73) Assignee: Gambro Lundia AB, Lund (SE)

( * ) Notice: Subject to any disclaimer, the term of this patent is extended or adjusted under 35 U.S.C. 154(b) by 246 days.

(21) Appl. No.: 12/307,670

(22) PCT Filed: Jun. 25, 2007

(86) PCT No.: PCT/EP2007/056325
§ 371 (c)(1),
(2), (4) Date: Jul. 6, 2009

(87) PCT Pub. No.: WO2008/003610
PCT Pub. Date: Jan. 10, 2008

(65) Prior Publication Data
US 2010/0012577 A1 Jan. 21, 2010

Related U.S. Application Data (60) Provisional application No. 60/806,948, filed on Jul. 11, 2006.

(30) Foreign Application Priority Data

Jul. 7, 2006 (EP) ..................................... 06116786

(51) Int. Cl.
*B01D 63/02* (2006.01)
*B01D 69/08* (2006.01)
*B01D 71/68* (2006.01)
*B01D 61/00* (2006.01)

(52) U.S. Cl. .............. 210/500.23; 210/500.41; 264/558; 264/561; 264/209.1; 264/211.14; 264/211.16; 264/41; 264/49

(58) Field of Classification Search ........................ None
See application file for complete search history.

(56) References Cited

U.S. PATENT DOCUMENTS

| 5,232,597 | A | * | 8/1993 | Eguchi ..................... 210/500.23 |
| 6,103,117 | A | * | 8/2000 | Shimagaki et al. ....... 210/321.71 |
| 6,163,363 | A | * | 12/2000 | Nelson et al. .................. 355/32 |
| 6,355,730 | B1 | | 3/2002 | Kozawa et al. |
| 2004/0050791 | A1 | | 3/2004 | Herczeg |
| 2007/0163949 | A1 | | 7/2007 | Wechs et al. |
| 2008/0000828 | A1 | | 1/2008 | Wechs et al. |

FOREIGN PATENT DOCUMENTS

| DE | 10 2004 008 220 A1 | 9/2005 |
| DE | 10 2004 008 221 A1 | 9/2005 |
| DE | 10 2004 008 219 B3 | 10/2005 |
| EP | 0 543 355 A2 | 5/1993 |

(Continued)

*Primary Examiner* — Krishnan S Menon
(74) *Attorney, Agent, or Firm* — Barnes & Thornburg LLP (57) ABSTRACT A process for manufacturing of an asymmetric hollow fiber membrane, comprising the steps of extruding a polymer solution through the outer ring slit of a hollow fiber spinning nozzle, simultaneously extruding a center fluid through the inner bore of the hollow fiber spinning nozzle, into a precipitation bath, whereby the polymer solution contains 10 to 26 wt-% of polysulfone (PSU), polyethersulfone (PES) or polyarylethersulfone (PAES), 8 to 15 wt-% polyvinylpyrrolidone (PVP), 55 to 75 wt-% N-alkyl-2-pyrrolidone (NAP) and 3 to 9 wt-% water the centre fluid contains 70 to 90 wt-% N-alkyl-2-pyrrolidone (NAP) and 10 to 30 wt-% water, and the precipitation bath contains 0 to 20 wt-% N-alkyl-2-pyrrolidone (NAP) and 80 to 100 wt-% water.

22 Claims, 6 Drawing Sheets

SEM micrographs of the inner surface of different microporous membranes. The concentrations given correspond to the solvent NMP (N-methyl-2-pyrrolidone) in wt-% in the centre fluid. The polymer composition used to make these membranes might vary. It is important to note that the magnification of the images is different. 68 %: Magnification 5000, the white bar indicates 7 µm; 75 %: Magnification 1010, the white bar indicates 30 µm; 80 %: Magnification 5000, the white bar indicates 7 µm; 92 %: Magnification 4020, the white bar indicates 8 µm.

FOREIGN PATENT DOCUMENTS

| | | |
|---|---|---|
| EP | 0 882 494 A1 | 12/1998 |
| EP | 1 547 628 A1 | 6/2005 |
| JP | 7-258915 | 10/1995 |
| WO | WO 2004/056460 A1 | 7/2004 |

* cited by examiner

Figure 1

SEM micrographs of the inner surface of different microporous membranes. The concentrations given correspond to the solvent NMP (N-methyl-2-pyrrolidone) in wt.-% in the centre fluid. The polymer composition used to make these membranes might vary. It is important to note that the magnification of the images is different. 68 %: Magnification 5000, the white bar indicates 7 μm; 75 %: Magnification 1010, the white bar indicates 30 μm; 80 %: Magnification 5000, the white bar indicates 7 μm; 92 %: Magnification 4020, the white bar indicates 8 μm.

Figure 2

Scanning Electron Micrographs (SEM) showing the morphology of the plasma separation membrane of the present invention.

Figure 3

Scanning electron micrographs of the cross section of the wall of the hollow fibre membrane of example 1 [Magnification 1490; the white bar indicates 20 μm] and the inner surface (blood contact) [Magnification 1010; the white bar indicates 30 μm].

Figure 4

Scanning electron micrograph of the inner surface (blood contact) of the hollow fibre membrane of example 2 [Magnification 2500; the white bar indicates 10 μm].

Figure 5

Scanning electron micrograph of the inner surface (blood contact) of the hollow fibre membrane of example 4 [Magnification 2500; the white bar indicates 10 μm].

Figure 6

Generation index of TCC for the Plasmaphan® and the Cuprophan® membrane (Membrana, Germany) and the membrane produced in Example 4. The TCC is measured in the plasma filtrated through the porous structure (not for Cuprophan; here measured in the pool) and correlated well with an increased TCC level in the pool. The experiment simulates a plasma therapy combined with a re-infusion of the treated plasma. It can be seen that both the Plasmaphan® plasma separation membrane as well as the Cuprophan® dialysis membrane show a strong activation level (TCC generation) compared to the membrane of Example 4 of the present invention.

PLASMA SEPARATION MEMBRANE

CROSS REFERENCE TO RELATED APPLICATIONS

This application is a national phase application based on PCT/EP2007/056325, filed Jun. 25, 2007, and claims the priority of European Patent Application No. 06116786.2, filed Jul. 7, 2006, and the benefit of U.S. Provisional Application No. 60/806,948, filed Jul. 11, 2006, the content of both of which is incorporated herein by reference.

BACKGROUND OF THE INVENTION

The present invention is directed to a process for manufacturing of an asymmetric hollow fibre membrane, which is, among other applications, particularly suitable for plasma separation, but which can also advantageously be used in certain technical applications. Furthermore this invention is directed to such membranes being producible by the process of the invention, and to the use of such membranes for plasma separation, plasma filtration, micro filtration, plasma therapy or cell filtration applications.

Plasma separation or apheresis is a medical technology in which the blood of a donor or patient is separated into the plasma, i.e. the cell free component in blood, and the blood cells. Plasma separation may be conducted for several reasons.

In the therapeutical plasmapheresis the separated plasma of a patient's blood is discarded and replaced by a substitute solution or by donor plasma, and is reinfused into the patient. This approach is useful in the treatment of several diseases and disorders. For example, in immunological diseases the plasmapheresis is useful to exchange antibodies, antigens, immune complexes or immune globulins. In non-immunological diseases the plasmapheresis allows for the depletion of metabolites, degradation products, as well as endogenous and exogenous toxins.

In a variant of therapeutical plasmapheresis, plasma fractionation, the separated plasma of a patient's blood undergoes a second stage of further separation into high molecular and low molecular plasma fractions. The high molecular fraction is discarded, and the low molecular fraction of the plasma and the cellular components of the blood are reinfused into the patient.

In an application, called plasma donation, the separated blood plasma from healthy donors is used for therapeutical plasma exchange, or for the isolation of plasma components for pharmaceutical purposes.

The separation of whole blood into plasma and cellular components can be achieved either by centrifugation or by passing the blood through a plasma separation membrane. During the development of plasmapheresis, discontinuous centrifuges have been used first, which have then, at the beginning of the 70s, been replaced by continuous centrifugation systems.

Centrifugation techniques have the advantage of being fast and cost effective, however, they often suffer from leaving impurities of cells or cell debris in the separated plasma. At the end of the 70s, the first membrane systems have been introduced for the plasmapheresis to overcome the disadvantages of centrifugation systems.

While being related to it, the requirements of plasma separation membranes are quite distinct from the requirements of dialysis membranes. Plasma separation uses the effect of separation by filtration, whereas dialysis rather uses osmosis and diffusion.

Some of the essential design criteria of a plasma separation membrane are the wall-shear rate, the transmembrane pressure drop and the plasma filtration rate.

The wall-shear rate in a hollow fibre membrane system is calculated by the following equation:

$$\gamma_w = \frac{4Q_B}{N\pi r^3}$$

wherein N is the number of hollow fibres, having the inner radius r, to which blood flow $Q_B$ is distributed. By the decrease of the plasma portion the blood flow changes across the length of the hollow fibre. This must be considered in the calculation of the wall-shear rate.

The transmembrane pressure (TMP) is another important parameter which is defined as the difference in pressure between the two sides of the membrane. The transmembrane pressure is the driving force for the membrane separation. In general, an increase in the transmembrane pressure increases the flux across the membrane. The exception to this generalization occurs if a compressible filter cake is present on the surface of the membrane. The transmembrane pressure is calculated by the following equation:

$$TMP = \frac{P_{Bi} + P_{Bo}}{2} - P_F$$

wherein $P_{Bi}$ is the pressure at the blood entrance, $P_{Bo}$ is the pressure at the blood exit, and $P_F$ is the pressure on the filtrate side of the membrane (plasma side).

The sieving coefficient determines how much of a compound will be eliminated by a filtration process. The sieving coefficient is defined as the ratio of the concentration of a compound in the filtrate to the concentration of this compound in the blood. A sieving coefficient of "0" means that the compound can not pass the membrane. A sieving coefficient of "1" means that 100% of the compound can pass the membrane. For the design of plasma separation membranes it is desired that the whole spectrum of plasma proteins can pass the filtration membrane whereas the cellular components are completely retained.

The requirements of a plasma separation membrane for plasmapheresis can be summarized as by the following characteristics:

- high permeability or high sieving coefficient for the whole spectrum of plasma proteins and lipoproteins;
- high surface porosity and total porosity of the membrane to achieve high filtration performance;
- a hydrophilic, spontaneously wettable membrane structure;
- low fouling properties for long term stable filtration;
- low protein adsorption;
- smooth surfaces in contact with blood;
- low or no tendency to haemolysis during blood processing;
- constant sieving properties and filtration behaviour over the whole treatment period;
- high biocompatibility, no complement activation, low thrombogenicity;
- mechanical stability;
- sterilizability by steam, gamma radiation and/or ETO;
- low amount of extractables.

DESCRIPTION OF THE INVENTION

The object of the present invention was to provide a novel hollow fibre membrane, particularly useful in plasma separation applications, having improved properties over the prior art membranes, especially in respect of the above-mentioned characteristics, and a process of producing such a membrane.

This and other objects are solved by a membrane being obtainable or obtained by the process of the present invention. Thus, according to the present invention there is provided a process for manufacturing of an asymmetric hollow fibre membrane, comprising the steps of extruding a polymer solution through the outer ring slit of a hollow fibre spinning nozzle, simultaneously extruding a centre fluid through the inner bore of the hollow fibre spinning nozzle, into a precipitation bath, whereby the polymer solution contains 10 to 26 wt-% of polysulfone (PSU), polyethersulfone (PES) or polyarylethersulfone (PAES), 8 to 15 wt-% polyvinylpyrrolidone (PVP), 55 to 75 wt-% N-alkyl-2-pyrrolidone (NAP) and 3 to 9 wt-% water the centre fluid contains 70 to 90 wt-% N-alkyl-2-pyrrolidone (NAP) and 10 to 30 wt-% water, and the precipitation bath contains 0 to 20 wt-% N-alkyl-2-pyrrolidone (NAP) and 80 to 100 wt-% water.

Even though some of the prior art membranes may, in comparison to the membrane produced according to the present invention, exhibit equal or similar characteristics in respect of one or several properties, the asymmetric hollow fibre membrane produced according to the present invention is superior in the combination of properties desired for a separation membrane, particularly a plasma separation membrane for plasmapheresis.

The asymmetric hollow fibre membrane produced according to the present invention exhibits high permeability for the whole spectrum of plasma proteins and lipoproteins, reflected by a high sieving coefficient. Preferably the sieving coefficient of the asymmetric hollow fibre membrane of the invention for all plasma proteins is >0.90, more preferably is >0.95.

The asymmetric hollow fibre membrane produced according to the present invention exhibits a high surface porosity and total porosity of the membrane to achieve high filtration performance. It further has a hydrophilic, spontaneously wettable membrane structure, low fouling properties for long term stable filtration, and low protein adsorption. The asymmetric hollow fibre membrane produced according to the present invention further has smooth surfaces in contact with blood which avoids or minimizes haemolysis during blood processing. The membrane shows constant sieving properties and filtration behaviour over the whole treatment period. It further exhibits high biocompatibility, low or no complement activation and low thrombogenicity. The mechanical stability of the membrane is excellent, and it is sterilizable by steam, gamma radiation and/or ETO.

In the process of the present invention it is required that the polymer solution contains 10 to 26 wt-% of polysulfone (PSU), polyethersulfone (PES) or polyarylethersulfone (PAES), whereby the use polyarylethersulfone (PAES) is most preferred. The polymer solution further contains 8 to 15 wt-% polyvinylpyrrolidone (PVP), 55 to 75 wt-% N-alkyl-2-pyrrolidone (NAP) and 3 to 9 wt-% water.

Using in the polymer solution less than 10 wt-% of polysulfone (PSU), polyethersulfone (PES) or polyarylethersulfone (PAES) causes the membrane to become very brittle compared to the membrane according to the present invention. At the same time the combination of desired membrane properties can not be achieved any longer. And, using more than 26 wt-% of polysulfone (PSU), polyethersulfone (PES) or polyarylethersulfone (PAES) this results in difficulties to prepare the polymer solution and to perform the spinning of hollow fibre membranes because of a too high viscosity of the polymer solution.

Using in the polymer solution less than 8 wt-% of polyvinylpyrrolidone (PVP) does not result in the required hydrophilicity (spontaneously wettable morphology) and the desired overall structure of the membrane. And, using more than 15 wt-% of polyvinylpyrrolidone (PVP) causes an extremely high viscosity of the polymer solution and complicates spinning of the hollow fibre membrane. At the same time the amount of extractables (PVP) increases very much. In addition to this, too high amounts of PVP lower the mechanical properties.

Using in the polymer solution less than 55 wt-% of N-alkyl-2-pyrrolidone (NAP) causes difficulties to process the polymer solution to form a membrane, due to an extremely high solution viscosity. And, using more than 75 wt-% N-alkyl-2-pyrrolidone (NAP) results in low solution viscosity. The polymer present in such a solution will not provide an ideal microporous membrane for plasma separation purposes.

In one embodiment of the process of the present invention the polymer solution contains 15 to 21 wt-% of polysulfone (PSU), polyethersulfone (PES) or polyarylethersulfone (PAES), 10 to 12.5 wt-% polyvinylpyrrolidone (PVP) and 60 to 70 wt-% N-alkyl-2-pyrrolidone (NAP).

In another embodiment of the process of the present invention the polymer solution contains 17 to 19 wt-% of polysulfone (PSU), polyethersulfone (PES) or polyarylethersulfone (PAES), 10.75 to 11.75 wt-% polyvinylpyrrolidone (PVP) and 63 to 66.5 wt-% N-alkyl-2-pyrrolidone (NAP).

In another embodiment of the process of the present invention the polymer solution contains 4 to 8 wt-% water. In yet another embodiment of the process of the present invention the polymer solution contains 5 to 7 wt-% water. In yet another embodiment of the process of the present invention the polymer solution contains about 6 wt-% water.

In the process of the present invention it is required that the centre fluid contains 70 to 90 wt-% N-alkyl-2-pyrrolidone (NAP) and 10 to 30 wt-% water.

Using in the centre fluid less that 70 wt-% N-alkyl-2-pyrrolidone (NAP) causes the membrane (i) to become too tight, i.e. the selective pore size of the membrane becomes too small to allow the majority of the plasma proteins to pass the membrane structure, or (ii) getting a high surface roughness which results in increased (unacceptable) haemolysis. And, using more than 90 wt-% N-alkyl-2-pyrrolidone (NAP) causes the membrane to get a rough surface causing haemolysis during blood treatment.

In one embodiment of the process of the present invention the centre fluid contains 73 to 87 wt-% N-alkyl-2-pyrrolidone (NAP) and 23 to 27 wt-% water.

In another embodiment of the process of the present invention the centre fluid contains 75 to 85 wt-% N-alkyl-2-pyrrolidone (NAP) and 15 to 25 wt-% water.

In the process of the present invention it is required that the precipitation bath contains 0 to 20 wt-% N-alkyl-2-pyrrolidone (NAP) and 80 to 100 wt-% water. Using in the precipitation bath more that 20 wt-% N-alkyl-2-pyrrolidone (NAP) causes the membrane to become instable during membrane formation.

In one embodiment of the process of the present invention the precipitation bath contains 0 to 10 wt-% N-alkyl-2-pyrrolidone (NAP) and 90 to 100 wt-% water.

In another embodiment of the process of the present invention the precipitation bath contains 0 to 5 wt-% N-alkyl-2-pyrrolidone (NAP) and 95 to 100 wt-% water.

In another embodiment of the process of the present invention the precipitation bath consists of pure water. In this context the phrase "consists of pure water" means that the precipitation bath at least at the start of the spinning operation consists of pure water without NAP, and it further means that any fresh liquid which is introduced into the precipitation bath also consists of pure water. However, it is also clear that during the spinning operation from the polymer solution and the centre fluid NAP is introduced into the precipitation bath which is dissolved in the precipitation bath and remains there to some extent. Depending on the size of the precipitation bath and the refresh rate, i.e. the rate of introducing fresh pure water into the bath, and the time of operation the NAP concentration can rise up to 10 wt-% in the precipitation bath.

In another embodiment of the process of the present invention the polymer solution extruded from the spinning nozzle is exposed to an atmosphere of a mixture of steam and humid air. The atmosphere of a mixture of steam and humid air, herein also called water vapour, surrounding the polymer solution extruded from the spinning nozzle stabilizes the membrane from the outside of the hollow fibre (precipitation of the polymer) and provides, at the same time, a very open structure on the outside of the membrane. Such structure of the surface on the outside of the hollow fiber membrane is achieved by modifying the spinning polymer solution composition only in the outer section of the hollow fiber membrane wall by penetration of water from the atmosphere of a mixture of steam and humid air into the first 1 to 15 μm of polymer solution layer just before the precipitation from the inside arrives at this layer. The penetration occurs in less than 0.5 seconds. The precipitation conditions allow achieving the desired membrane structure.

Technically there are three options to provide an atmosphere of water vapour surrounding the fibre leaving the spinning nozzle: (A) using the water vapour generated by the hot water bath and having the spinning die only a few centimetres above the surface of the precipitation bath, (B) using a spinning shaft, i.e. a small metal or plastic housing surrounding the fibre leaving the spinning die, which housing extends from the spinning die or spinning head, respectively, and ends at a close distance above the surface of the precipitation bath to have the steam partly concentrated in the volume around the fibre travelling from the spinning die to the precipitation bath, or (C) using steam supplied from an external source, optionally in combination with a spinning shaft as described for option (B).

Thus, in another embodiment of the process of the present invention the steam and/or humid air is provided from an external source and introduced into the atmosphere surrounding the polymer solution extruded from the spinning nozzle.

Further, in another embodiment of the process of the present invention there is provided a spinning shaft extending from the spinning nozzle or spinning head and ending (opening) at a distance above the surface of the precipitation bath, whereby the spinning shaft along its length surrounds the polymer solution extruded from the spinning nozzle and traveling to the precipitation bath.

In another embodiment of the process of the present invention the spinning shaft has a cylindrical shape or a rectangular shape.

In another embodiment of the process of the present invention the spinning shaft has a length of 1 to 20 cm, preferably 3 to 13 cm, most preferably 5 to 7 cm.

In another embodiment of the process of the present invention the temperature of the mixture of steam and humid air is at least 15° C., preferably at least 30° C., and at most 75° C., preferably at most 60° C.

In another embodiment of the process of the present invention the humidity in the atmosphere of the mixture of steam and humid air is between 60 and 100%.

In another embodiment of the process of the present invention the atmosphere of the mixture of steam and humid air comprises a solvent in a content of between 0.5 and 5%. Such solvent content in the atmosphere may be provided from evaporation of solvent in the precipitation bath or from evaporation of solvent in the polymer solution during fibre formation.

In the process of the present invention the N-alkyl-2-pyrrolidone (NAP) in the polymer solution, in the centre fluid and in the precipitation bath, if present, can be the same or different, however most preferably is the same in all three solutions.

Preferably the N-alkyl-2-pyrrolidone (NAP) is selected from the group consisting of N-methyl-2-pyrrolidone (NMP), N-ethyl-2-pyrrolidone (NEP), N-octyl-2-pyrrolidone (NOP) or mixtures thereof, whereby N-methyl-2-pyrrolidone (NMP) is most preferred.

In another embodiment of the process of present invention the polyvinylpyrrolidone (PVP) in the polymer solution consists of a blend of at least two homo-polymers of polyvinylpyrrolidone whereby one of the homo-polymers of polyvinylpyrrolidone (=low molecular weight PVP) having an average relative molecular weight of about 10.000 g/mole to 100.000 g/mole, preferably about 30.000 g/mole to 60.000 g/mole, and another one of the homo-polymers of polyvinylpyrrolidone (=high molecular weight PVP) having an average relative molecular weight of about 500.000 g/mole to 2.000.000 g/mole, preferably about 800.000 g/mole to 2.000.000 g/mole. It is even more preferred if the polyvinylpyrrolidone (PVP) in the polymer solution consists of a blend of only two homopolymers of polyvinylpyrrolidone of the afore-mentioned type.

Using a blend of two homo-polymers of polyvinylpyrrolidone of different average relative molecular weights results in a desired hydrophilicity, structure and morphology of the membrane. Without being bound by theory, it is assumed that during the production process the high molecular weight PVP remains incorporated in the hollow fibre membrane, whereas the majority of the low molecular weight PVP is washed out.

In one embodiment of the invention the low molecular weight PVP in the polymer solution is present in an amount of 5.7 to 11.7 wt-% and the high molecular weight PVP is present in an amount of 2.3 to 4.3 wt-%, based on the total weight of the polymer solution. In another embodiment the low molecular weight PVP is present in an amount of 7.1 to 8.9 wt-% and the high molecular weight PVP is present in an amount of 2.9 to 3.6 wt-%, based on the total weight of the polymer solution. In a further embodiment the low molecular weight PVP is present in an amount of about 3.25 wt-% and the high molecular weight PVP is present in an amount of about 8.0 wt-%, based on the total weight of the polymer solution. The total amount of PVP should, however, be within the ranges indicated above. If the concentration of high molecular weight PVP is too low, then the degree of hydrophilicity of the membrane might not be sufficient. If the concentration of high molecular weight PVP is too high, then the viscosity of the polymer solution might be too high causing serious processability problems. If the concentration of low molecular weight PVP is too low, then this results in a closed cell structure instead of an open membrane structure. If the concentration of low molecular weight PVP is too high, then this would require the removal of the low molecular weight PVP by exhaustive washing. If too much of the low molecular weight PVP remains in the membrane product the membrane could not be used for blood treatment because the extractable PVP would contaminate the blood or plasma.

In another embodiment of the invention the precipitation bath (PB) has a temperature in the range 30 to 100° C., preferably 40 to 90° C., most preferably 50 to 80° C. If the temperature of the precipitation bath in this embodiment is too low the precipitation of the membrane might be too slow, which could result in a too dense structure on the outside. If the temperature of the precipitation bath in this embodiment is too high the fibre becomes instable during the precipitation procedure.

In another embodiment of the process of the present invention the hollow fibre spinning nozzle (die; spinneret) is held at a temperature in the range 10 to 90° C., preferably 20 to 80° C., more preferably 40 to 60° C., most preferably at about 50° C. If the temperature of the hollow fibre spinning nozzle is too low the pressure drop in the spinning die is increasing. The pressure drop increases exponentially if die temperature is lowered. A high pressure drop results in unstable spinning conditions, i.e. rougher outer surface, increased variations in dimension etc. If the temperature of the hollow fibre spinning nozzle is too high the speed of polymer outflow out of the die might be too fast. This would result in unstable spinning conditions.

In another embodiment of the process of the present invention the distance (gap) between the discharge outlet of the hollow fibre spinning nozzle (die; spinneret) to the surface of the precipitation bath is in the range of 0.5 to 20 cm, preferably 1 to 15 cm, more preferably 5 to 10 cm, most preferably 7 to 9 cm. If the distance between the discharge outlet of the hollow fibre spinning nozzle to the surface of the precipitation bath is too low the desired product properties will not be achieved, e.g. an open and smooth outer surface in combination with an open structure in the membrane wall. If the distance between the discharge outlet of the hollow fibre spinning nozzle to the surface of the precipitation bath is too high the spinning becomes difficult or even impossible. The stability of the fibre is not provided if the distance is increased above the given limit.

In another embodiment of the process of the present invention the spinning speed of the hollow fibre membrane is in the range of 1 to 40 m/min, preferably 3 to 40 m/min, more preferably 5 to 20 m/min, most preferably about 13 m/min. If the spinning speed of the hollow fibre membrane is too low the spinning conditions become unstable and the desired membrane dimensions cannot be achieved. If the spinning speed of the hollow fibre membrane is too high the residence time for the fibre to be subjected to a steam or humid air environment is decreasing, which results in extremely dense layers in the cross section. These dense layers do not allow a sufficiently high sieving coefficient for all plasma proteins.

In another embodiment of the process of the present invention the polymer solution has a viscosity, measured at room temperature, of 30.000 to 100.000 mPa×s (Centipoise). If the viscosity is lower than 30.000 mPa×s (Centipoise) then the stability of the fiber in the precipitation bath is not provided, which results in fiber breaking during the spinning process. If the viscosity is higher than 100.000 mPa×s (Centipoise) then solution handling, i.e. solution preparation and pumping of the solution becomes difficult, and the pressure drop in the spinning die becomes too high.

The present invention covers also hollow fibre membranes obtainable or obtained by the process of the invention.

In one embodiment of the present invention the hollow fibre membrane is characterized by a total plasma protein sieving coefficient of >0.90, preferably >0.95. A high sieving coefficient for total plasma protein is essential to the membrane if it is used for example as a plasma separation membrane. In plasma separation it is desired to have the total plasma protein in the separated plasma fraction, whereas the larger corpuscular components of the blood, like blood cells and cell debris, are retained by the membrane.

For plasma separation applications it is preferred that the hollow fibre membrane shall have an inner diameter in the range of 100 to 500 μm, preferably 150 to 450 μm, more preferably 200 to 400 μm. Lower inner diameters are disadvantageous because they result in too high wall shear rates and increased pressure drop in the fibre or in the whole filtration module. On the other hand, if the inner diameters are too high, this would result in too low shear rates which increase the risk of haemolysis at low transmembrane pressures (TMP).

It is further preferred for plasma separation applications that the hollow fibre membrane shall have a wall thickness in the range of 20 to 150 μm, preferably 30 to 125 μm, more preferably 40 to 100 μm. Lower wall thicknesses are disadvantageous due to reduced mechanical properties of the fibre during production and during its use in the plasma separation module itself. Higher wall thicknesses are disadvantageous because they require increased time intervals to perform the phase inversion process resulting in instable process conditions and an instable membrane.

It is further preferred for plasma separation applications that the hollow fibre membrane shall have an average pore diameter of the selective separation layer in the membrane in the range of 0.1 to 1 μm, preferably 0.1 to 0.7 μm, more preferably 0.1 to 0.4 μm. Lower average pore diameters of the selective separation layer are disadvantageous due to incomplete passage of total plasma proteins through the porous structure.

In another embodiment of the present invention the hollow fibre membrane is characterized by a pore size distribution wherein the pore sizes at a distance between the inner wall surface of the membrane (lumen surface) and the outer wall surface of the membrane is smallest and increasing towards the inner wall surface and the outer wall surface, respectively.

The process of the present invention for the manufacturing of microporous membranes, particularly plasma separation membranes, is a diffusion induced phase separation (DIPS) procedure. The average diameter of the selective pores of such plasma separation membranes is in the range of 0.1 to 0.4 μm. The porous structure next to the "selective" pore size region has larger pores up to several μm. To achieve such larger pores next to the selective layer of the structure the phase separation process has to be performed slowly to allow generation of the pores beginning with a pore size of approximately 0.1 μm and larger or using steam on one side of the membrane wall. To allow a slow phase separation process the amount of solvent for the polymer, in our case NAP (N-alkyl-2-pyrrolidone), preferably NMP (N-methyl-2-pyrrolidone), has to be sufficiently high in the centre fluid.

One of the major findings of the present invention was that increasing the amount of NAP in the centre fluid leads to an increase in pore size at the inner layer. Further, it was found that increasing the amount of NAP in the centre fluid from e.g.

Figure 1:
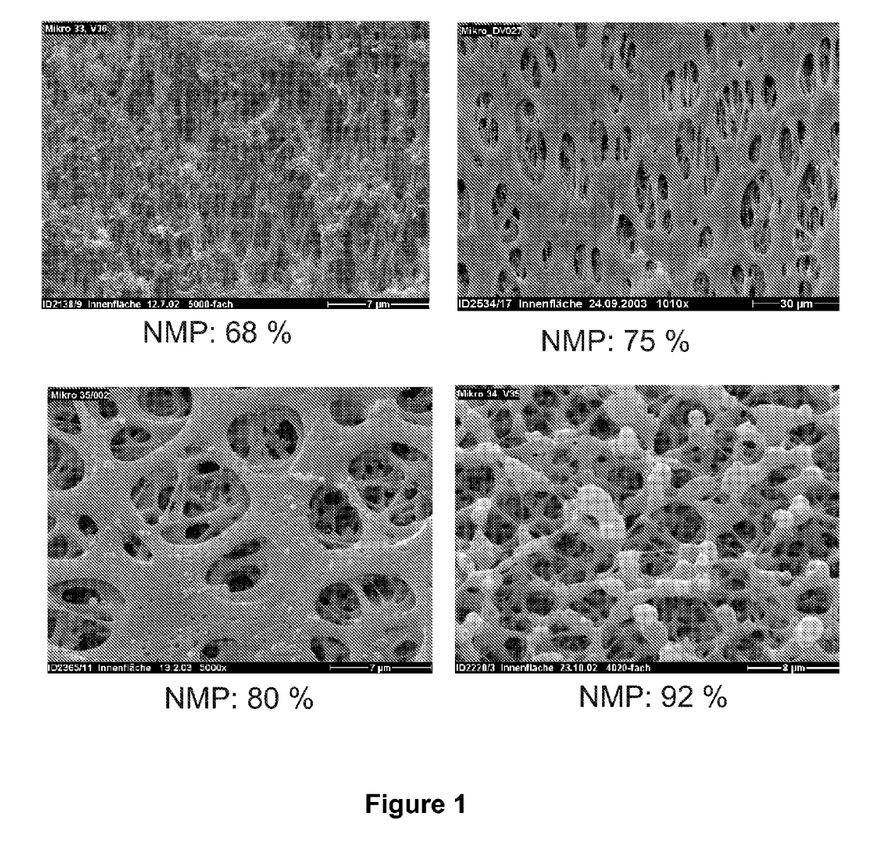
FIG. 1: SEM of the inner surface of different microporous membranes.

60 wt-% or below to about 68 wt-% leads to an increase of the roughness of the inner surface of the hollow fibre membrane. Surprisingly, further increasing the amount of NAP in the centre fluid leads to a decrease of the roughness again. Then, above a certain concentration of NAP of about 90 wt-% the roughness extremely increases again. This is a phenomenon one would not expect normally. Thus, in a narrow concentration range window between 70 to 90 wt-% of NAP in the centre fluid a smooth surface can be achieved (see FIG. 1).

Pore size and surface roughness are two essential parameters of the separation membrane of the present invention. A sufficiently large pore size is important to achieve the required plasma protein passage (high sieving coefficient). The width of the pore size distribution is also of major importance to allow all plasma proteins to pass this membrane. However, increasing the NAP concentration in the centre fluid to achieve larger pore sizes leads to a slower phase separation procedure (slower precipitation and slower membrane structure formation), which results in decreased stability of the membrane. Further, the roughness of the inner membrane surface should be kept as low as possible to minimize or avoid haemolysis. The challenge was to find a production window that allows to adjust (i) sufficient high concentration of NAP in the centre fluid to generate a morphology that allows all plasma proteins to pass, (ii) acceptable roughness to have no or reduced haemolysis, (iii) a composition of the precipitation bath and the steam or humid air atmosphere above the precipitation bath to get a sufficient open structure on the outside and in the cross section, (iv) stable spinning conditions.

The present inventors have now identified a process route allowing the production of plasma separation membranes fulfilling the desired property profile.

Figure 2:
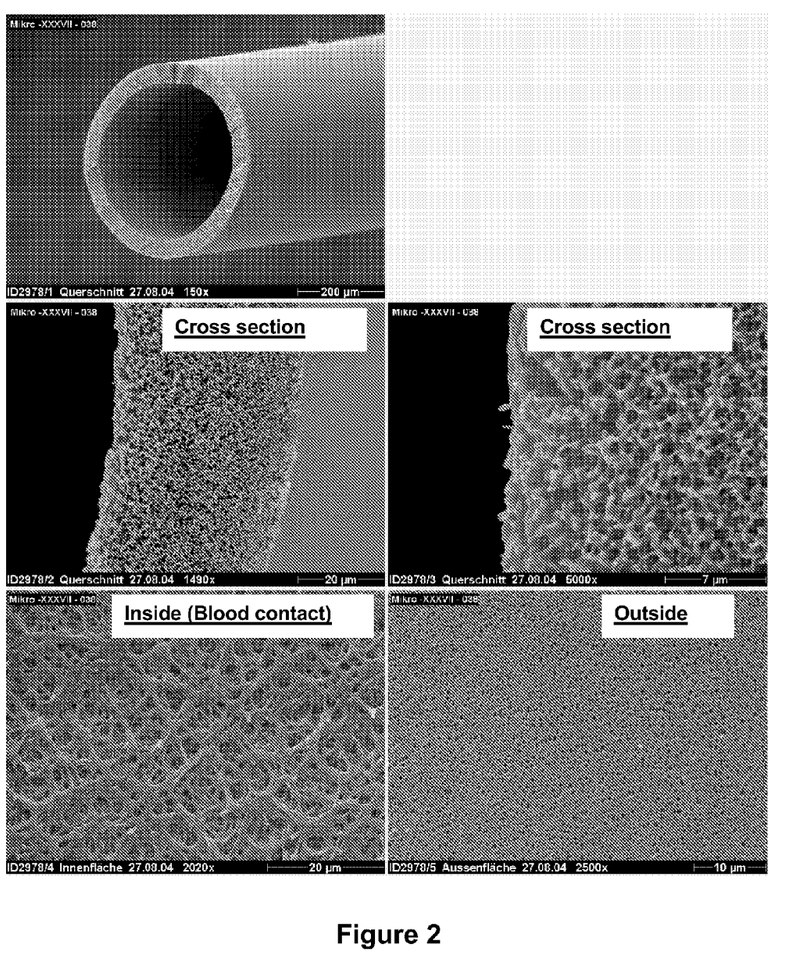
FIG. 2: SEM showing the morphology of the plasma separation membrane of the present invention.

An example of preferred process conditions for the production of a plasma separation membrane according to the present invention is displayed in Table 1. The polymer solution is pumped through a spinning die and the liquid hollow fibre is formed. The NMP concentration in the centre fluid leads to a microporous open structure at the inner side of the membrane. The smallest pores (selective layer) are not at the blood contacting surface but rather somewhere in the cross section of the membrane. The composition of the precipitation bath together with the atmosphere of water vapour surrounding the polymer solution extruded from the spinning nozzle leads to a very open outside and overall (cross section) structure. The overall structure and the pores at the outside of the membrane are much bigger (see FIG. 2) The challenge of the invention was to adjust the spinning conditions to fulfil the profile of the membrane, i.e. biocompatibility, haemolysis and high sieving coefficient and high filtration rate over time.

TABLE 1

Conditions for the production of a plasma separation membrane of the present invention.

| | | |
|---|---|---|
| Composition of the polymer solution [wt-%] | PAES: | 18% |
| | PVP (high mol. weight): | 3.25% |
| | PVP (low mol. weight): | 8% |
| | NMP: | 64.75% |
| | Water | 6% |
| Composition of the centre fluid [wt-%] | H$_2$O: | 22% |
| | NMP: | 78% |
| Composition of the precipitation bath [wt-%] | NMP: | 0% |
| | Water | 100% |
| Temperature of the precipitation bath [° C.] | 50° C. | |
| Distance between die and precipitation bath [cm] | 8 cm | |

TABLE 1-continued

Conditions for the production of a plasma separation membrane of the present invention.

| | |
|---|---|
| Temperature of the die [° C.] | 50° C. |
| Spinning speed [m/min] | 13 m/min |
| Viscosity [mPa × s] | 63.600 mPa × s |

Materials and Methods

Viscosity Measurement

The term "viscosity" in respect of the polymer solution of the present invention means the dynamic viscosity, if not otherwise indicated. The Unit of the dynamic viscosity of the polymer solution is given in Centipoise (cp) or mPa×s. To measure the viscosity of the polymer solution a commercial Rheometer from Rheometric Scientific Ltd. (SR 2000) was used. The polymer solution is placed between two temperature-controlled plates. The measurement is performed at 22° C. All other measurement condition are according to the manufacturer's instructions.

Membrane Bundle Preparation a) Preparation of Hand Bundles:

The preparation of membrane bundles after the spinning process is necessary to prepare the fibre bundle in an adequate way for the performance tests (measurement of the total protein sieving coefficient and determination of the haemolysis properties of the membrane). The first process step is to fix the fibres near their ends by a filament. The fibre bundle is transferred into a sterilization tube and then sterilized. After the sterilization, the fibre bundle is cut to a defined length of 23 cm. The next process step consists of closing the ends of the fibres. An optical control ensures that all fibres are well closed. Then, the ends of the fibre bundle are transferred into a potting cap. The potting cap is fixed mechanically, and a potting tube is put over the potting caps. Afterwards, the potting is done with polyurethane. After the potting, it has to be ensured that the polyurethane can harden for at least one day. In the next process step, the potted membrane bundle is cut to a defined length. The last process step consists of an optic control of the fibre bundle. During this process step, the quality of the cut (is the cut smooth or are there any damages of the knife) and the quality of the potting (is the number of open fibres of the spinning process reduced by fibres that are potted or are there any visible voids where the there is no polyurethane) are controlled. After the optical control, the membrane bundles are stored dry before they are used for the different performance tests.

b) Preparation of Minimodules:

Minimodules, i.e. fibre bundles in a housing, are prepared by similar process steps as in the preparation of hand bundles. The minimodules are needed to ensure a protection of the fibres and a very clean manufacturing method as the biocompatibility tests are carried out with human plasma. The manufacturing of the minimodules differs in the following points over the preparation of hand bundles in that i) the fibre bundle is cut to a defined length of 20 cm, ii) the fibre bundle is transferred into the housing before the fibres are closed, and iii) the minimodule is put into a vacuum drying oven over night before the potting process.

Total Protein Sieving Coefficient

The total protein sieving coefficient of a membrane is determined by pumping bovine blood with a defined haematocrit under defined conditions (shear rate [by adjusting the $Q_B$], TMP) through a membrane bundle and determining the concentration of the total protein in the feed, in the retentate and in the filtrate. If the concentration of the total protein in the filtrate is zero, a sieving coefficient of 0% is obtained. If the concentration of the total protein in the filtrate equals the concentration of the protein in the feed and the retentate, a sieving coefficient of 100% is obtained. The sampling takes place at the earliest 10 minutes after a constant TMP is adjusted. The test is carried out in the single-pass modus. The bovine blood is heated up by a heat exchanger to 37° C. before entering the fibre bundle. The retentate and the feed samples are centrifuged before the determination of the concentration of the total protein. The determination of the total protein is done photometric. The test can be modified to determine the long-term stability of the total protein sieving coefficient. In this case, a constant TMP is applied over a longer time schedule.

Haemolysis Test

The haemolysis test is carried out in a similar way as the sieving coefficient test described before. The applied transmembrane pressures are in the range of 30 to 150 mmHg. Before the sampling, at least 10 minutes are waited to ensure an equilibrated situation. After the test, the pool samples are centrifuged; no retentate samples are taken for the determination of the free haemoglobin. The determination of the free haemoglobin is done photometric. The value of the free haemoglobin in the filtrate is adjusted with the value in the pool sample to receive the content of free haemoglobin generated by the membrane. In parallel, a standard curve is created to get the correlation between the measured optical density to the content of free haemoglobin. The standard curve is prepared by diluting one ml of bovine blood directly at the beginning with 9 ml of distilled water. After centrifugation, 1 ml of the supernatant is taken and is diluted with 9 ml of isotonic sodium chloride solution. This represents the 1% standard. Starting with this 1% standard a series of further concentrations in the range of 0.05 to 1% are produced by dilution. Using these concentrations the standard curve is created by measuring the corresponding optical density. A level of haemoglobin below 0.2 in the generated plasma fraction is characterized as "non" or "low" haemolytic. Concentrations above 0.2 can be identified visually (colour change) as haemolytic. Detailed measurements are performed photometrically.

Biocompatibility Testing

The following two methods are used to characterize the biocompatibility properties of the membrane:

a) Thrombogenicity:

Thrombin-Antithrombin III (TAT) levels are measured and platelet counts are done after passage of platelet rich plasma (PRP) along the membrane, through the membrane and in the pool as a marker for thrombogenicity. The experiment is carried out in a recirculating modus as a high volume of plasma is required to test in the "single pass modus".

b) Complement Activation:

Complement activation, as generated by the terminal complement complex (TCC), is measured before and after the passage of fresh human plasma through the minimodule. Additionally, the generation of TCC in the filtrate is measured. The experiment is carried out in a recirculating modus, since a high volume of plasma is required to test in the "single pass modus". The details of the complement activation measurement are as described by Deppisch, R., et al., *Fluid Phase Generation of Terminal Complement Complex as a Novel Index of Biocompatibility*. Kidney International, 1990.37: p. 696-706.

Complement activation is not only related to cellular activation but also to the activation of the plasmatic fraction. In the case of plasma separation and subsequent treatment, for example adsorption, double filtration complement activation becomes a major issue. In case of increased complement activation, i.e. generation of TCC, the activated plasma may cause severe health problems to a patient, if it is re-infused into a patient.

EXAMPLES

Example 1

A polymer solution was prepared by dissolving 18.0 wt-% polyethersulfone (PES; BASF Ultrason 6020), 3.25 wt-% low molecular weight polyvinylpyrrolidone (PVP; BASF K30) and 8.0 wt-% high molecular weight polyvinylpyrrolidone (PVP; BASF K85 or K90) and 6.0 wt-% water in 70.75 wt-% N-methylpyrrolidone (NMP). The viscosity of the polymer solution at room temperature was 61810 mPa×s.

To prepare the solution, NMP and the water were placed in a three neck-flask with finger-paddle agitator in the centre neck. Then, the PVP was added to the NMP and stirred at 50° C. until a homogeneous clear solution was formed. Finally, the polyethersulfone (PES) was added. The mixture was stirred at 50° C. until a clear high viscous solution is obtained. The warm solution was cooled down to 20° C. and degassed. To fully degas the solution the highly viscous polymer solution was transferred into a stable stainless steel container, the container was closed tightly and vacuum was applied to the container. The solution was degassed at 50 mmHg for 6 hours. During this degassing procedure the container was moved to create a larger surface and thinner film thickness of the polymer solution in the container to improve the degassing procedure.

To form a membrane the polymer solution was heated up to 50° C. and passed through a spinning die into a precipitation bath. As centre fluid a mixture of 25.0 wt-% water and 75.0 wt.-% NMP was used. The temperature of the die was 45° C. The hollow fibre membrane was formed at a spinning speed of 13 m/min. The liquid capillary leaving the die was passed into a heated water bath (precipitation bath) having a temperature of 85° C. Vapour created by the heat water bath surrounded the fibre. The distance between the exit of the die and the precipitation bath was 5 cm. The formed hollow fibre membrane was guided through 5 different water baths having a temperature of 65° C. Finally, the membrane was wound onto a winding-up equipment. The fibres were transferred into bundles and washed with water at 75° C. to remove traces of NMP and water soluble polymer residuals.

The resulting hollow fibre membrane had an inner diameter of 328 μm, an outer diameter of 426 μm and a fully asymmetric membrane structure. The measured total protein sieving coefficient was 100% at the transmembrane pressures (TMP) of 30, 70 and 110 mmHg (Mean Blood flow $Q_B$: 4.1 ml/min, mean shear rate: 260 1/s). The degree of free haemoglobin as the corrected filtrate value (see description of methods) was below the border of starting haemolysis of 0.2 for the tested values of 30, 70 and 110 mmHg.

Figure 3:
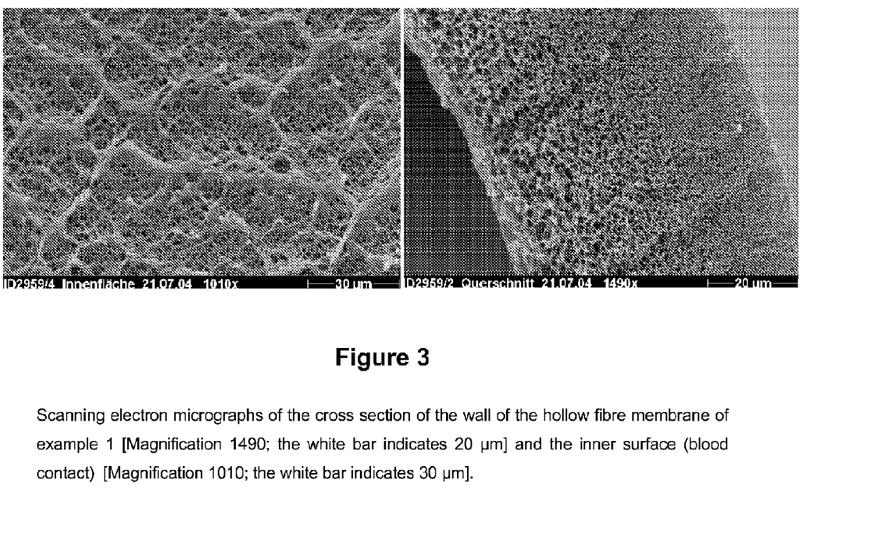
FIG. 3: SEM of the cross section of the wall of the hollow fiber membrane of example 1.

Scanning electron micrographs of the inner surface and the cross section of the membrane are shown in FIG. 3. The membrane wall shows an asymmetric structure having an overall sponge like structure. The inner surface shows a relative smooth surface.

Example 2

In Example 2 the same compositions of the polymer solution and the precipitation bath were used as in Example 1. The viscosity of the polymer solution at room temperature was 62500 mPa×s. As centre fluid a mixture of 20.0 wt.-% water and 80.0 wt.-% NMP was used. The membrane formation procedure was the same as in Example 1 with the exceptions that the temperature of the die was 50° C., distance between the die and the precipitation bath was 4 cm, and the temperature of the precipitation bath was 50° C.

The resulting hollow fibre membrane had an inner diameter of 320 µm, an outer diameter of 420 µm and a fully asymmetric membrane structure. The total protein sieving coefficient was 100% at a transmembrane pressure (TMP) of 50 mmHg (Mean Blood flow $Q_B$: 3.1 ml/min, mean shear rate: 255 1/s). The degree of free haemoglobin as the corrected filtrate value was below the border of starting haemolysis of 0.2 for the tested value of 50 mmHg.

Figure 4:
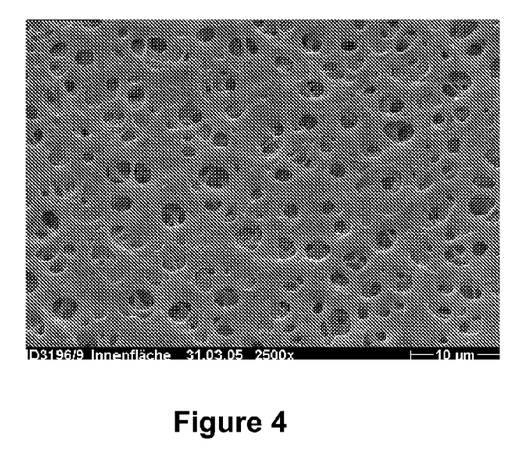
FIGS. 4 and 5: SEM of the inner surface of the hollow fiber membrane of examples 2 and 4 respectively.

A scanning electron micrograph of the inner surface is shown in FIG. 4. The inner surface shows a very smooth surface.

Example 3

In Example 3 the same compositions of the polymer solution and the precipitation bath were used as in Example 1. The viscosity of the polymer solution at room temperature was 62500 mPa×s. As centre fluid a mixture of 22.0 wt.-% water and 78.0 wt.-% NMP was used. The membrane formation procedure was the same as in Example 1 with the exceptions that the temperature of the die was 50° C., distance between the die and the precipitation bath was 8 cm, and the temperature of the precipitation bath was 50° C. Further, in addition to examples 1 and 2 the liquid fibre leaving the spinning die passed a spinning shaft of 6 cm length extending from the exit of the die to a distance of about 2 cm above the surface of the precipitation bath. The spinning shaft provided for a space of a conditioned atmosphere of steam or humid air surrounding the fibre when travelling from the exit of the spinning die into the precipitation bath. The steam or humid air was thereby generated by evaporation of water from the precipitation bath. In this example, no additional steam was supplied from an external source.

The resulting hollow fibre membrane had an inner diameter of 318 µm, an outer diameter of 422 µm and a fully asymmetric membrane structure. The total protein sieving coefficient was 100% at a transmembrane pressures (TMP) of 50, 100 and 150 mmHg (Mean Blood flow $Q_B$: 3.0 ml/min, mean shear rate: 250 1/s). Additionally, the long term stability of the total protein sieving coefficient was determined at a TMP of 50 mmHg. The total protein sieving coefficient was 100% after 15 minutes and 95% after 60 minutes. The degree of free haemoglobin as the corrected filtrate value (compare description of the method) was below the border of starting haemolysis of 0.2 for the tested value of 30 mmHg.

Thrombogenicity measurements were carried out, and the produced membrane showed excellent thrombogenicity properties (data not shown).

Example 4

In Example 4 the same compositions of the polymer solution and the precipitation bath were used as in Example 1. The viscosity of the polymer solution at room temperature was 51400 mPa×s. As centre fluid a mixture of 22.0 wt.-% water and 78.0 wt.-% NMP was used. The membrane formation procedure was the same as in Example 1 with the exceptions that the temperature of the die was 55° C., the distance between the die and the precipitation bath was 4 cm, and the temperature of the precipitation bath was 80° C. Further, in addition to examples 1 and 2 the liquid capillary leaving the die passed a spinning shaft having a length of 2 cm into the precipitation bath.

The resulting hollow fibre membrane had an inner diameter of 319 µm, an outer diameter of 417 µm and a fully asymmetric membrane structure. The total protein sieving coefficient was 97% at a transmembrane pressure (TMP) of 50 mmHg and 100% at a transmembrane pressure (TMP) of mmHg (Mean Blood flow $Q_B$: 3.2 ml/min, mean shear rate: 2651/s). The degree of free haemoglobin as the corrected filtrate value (compare description of the method) was below the border of starting haemolysis of 0.2 for the tested values of 50 and 100 mmHg.

Figure 5:
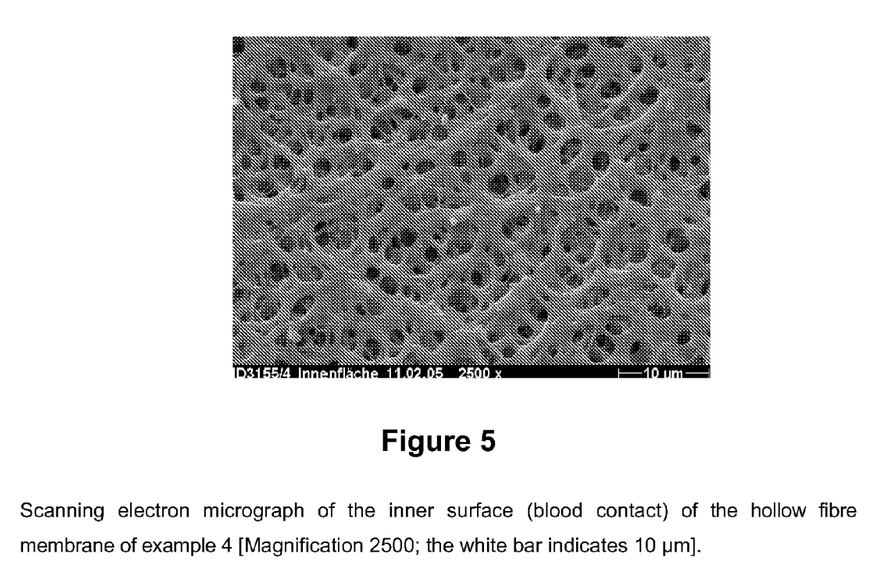

A scanning electron micrograph of the inner surface is shown in FIG. 5. The inner surface shows a very smooth surface.

Figure 6:
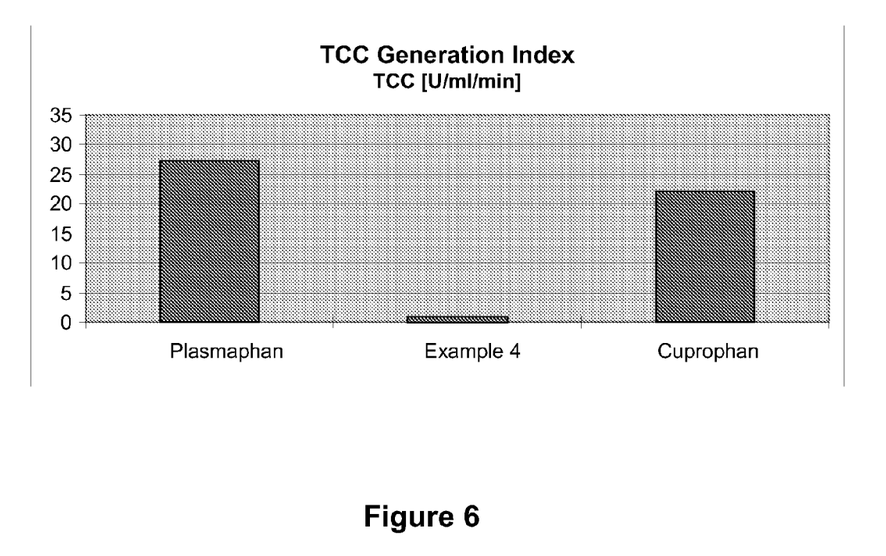
FIG. 6: TCC generation index.

Complement activation was measured with micromodules in comparison to the Plasmaphane® and Cuprophane® membranes (Membrana, Germany). FIG. 6 demonstrates the results. The TCC values of the membrane produced in Example 4 were very low compared to the Plasmaphane® and Cuprophane® membranes.

The invention claimed is:

1. A process for manufacturing an asymmetric hollow fiber membrane, comprising the steps of extruding a polymer solution through an outer ring slit of a hollow fiber spinning nozzle and simultaneously extruding a center fluid through an inner bore of the hollow fiber spinning nozzle into a precipitation bath, whereby the polymer solution contains 10 to 26 wt-% of polysulfone, polyethersulfone, or polyarylethersulfone, 8 to 15 wt-% polyvinylpyrrolidone, 55 to 75 wt-% N-alkyl-2-pyrrolidone and 3 to 9 wt-% water; the center fluid contains 70 to 90 wt-% N-alkyl-2-pyrrolidone and 10 to 30 wt-% water; and the precipitation bath contains 0 to 20 wt-% N-alkyl-2-pyrrolidone and 80 to 100 wt-% water.

2. The process of claim 1, wherein the polymer solution contains 15 to 21 wt-% of polysulfone, polyethersulfone, or polyarylethersulfone, 10 to 12.5 wt-% polyvinylpyrrolidone, and 60 to 70 wt-% N-alkyl-2-pyrrolidone.

3. The process of claim 1, wherein the polymer solution contains 4 to 8 wt-% water.

4. The process of claim 1, wherein the center fluid contains 73 to 87 wt-% N-alkyl-2-pyrrolidone and 23 to 27 wt-% water.

5. The process of claim 1, wherein the precipitation bath contains 0 to 10 wt-% N-alkyl-2-pyrrolidone and 90 to 100 wt-% water.

6. The process of claim 1, wherein the N-alkyl-2-pyrrolidone in the polymer solution, in the center fluid, and in the precipitation bath, if present, may be the same or different, and is selected from the group consisting of N-methyl-2-pyrrolidone, N-ethyl-2-pyrrolidone, N-octyl-2-pyrrolidone or mixtures thereof.

7. The process of claim 6, wherein the N-alkyl-2-pyrrolidone in the polymer solution, in the center fluid, and in the precipitation bath, if present, is the same and is N-methyl-2-pyrrolidone.

8. The process of claim 1, wherein the polyvinylpyrrolidone in the polymer solution consists of a blend of at least two homo-polymers of polyvinylpyrrolidone, whereby one of the homo-polymers of polyvinylpyrrolidone has a low molecular weight with an average relative molecular weight of about 10,000 g/mole to 100,000 g/mole, and another one of the homo-polymers of polyvinylpyrrolidone has a high molecular weight with an average relative molecular weight of about 500,000 g/mole to 2,000,000 g/mole.

9. The process of claim 8, wherein in the polymer solution, based on the total weight of the polymer solution, the low molecular weight homo-polymer of polyvinylpyrrolidone is present in an amount of 5.7 to 11.7 wt-% and the high molecular weight homo-polymer of polyvinylpyrrolidone is present in an amount of 2.3 to 4.3 wt-%.

10. The process of claim 1, wherein the precipitation bath has a temperature in the range 30 to 100° C.

11. The process of claim 1, wherein the hollow fiber spinning nozzle is held at a temperature in the range 10 to 90° C.

12. The process of claim 1, wherein a distance between the discharge outlet of the hollow fiber spinning nozzle to the surface of the precipitation bath is in the range of 0.5 to 20 cm.

13. The process of claim 1, wherein a spinning speed of the hollow fiber membrane is in the range of 1 to 40 m/min.

14. The process of claim 1, wherein the polymer solution has a viscosity, measured at room temperature, of 30,000 to 100,000 mPa×s (Centipoise).

15. The process of claim 1, wherein the polymer solution extruded from the spinning nozzle is exposed to an atmosphere of a mixture of steam and humid air.

16. The process of claim 15, wherein the temperature of the mixture of steam and humid air is at least 15° C. and at most 75° C.

17. The process of claim 15, wherein the humidity in the atmosphere of the mixture of steam and humid air is between 60 and 100%.

18. The process of claim 15, wherein the atmosphere of the mixture of steam and humid air comprises a solvent in a content of between 0.5 and 5%.

19. The process of claim 15, wherein either steam or humid air, or both, is provided from an external source and introduced into the atmosphere surrounding the polymer solution extruded from the spinning nozzle.

20. The process of claim 1, wherein a spinning shaft extends from the spinning nozzle or spinning head and ends at a distance above the surface of the precipitation bath, whereby the spinning shaft along its length surrounds the polymer solution extruded from the spinning nozzle and traveling to the precipitation bath.

21. The process of claim 20, wherein the spinning shaft has a cylindrical shape or a rectangular shape.

22. The process of claim 20, wherein the spinning shaft has a length of 1 to 20 cm.

* * * * *